(12) United States Patent
BenMohamed et al.

(10) Patent No.: US 9,878,033 B2
(45) Date of Patent: Jan. 30, 2018

(54) IMMUNOGENIC PEPTIDES FOR TREATMENT OF HERPES SIMPLEX VIRUS INFECTION AND CONDITIONS

(71) Applicant: The Regents of the University of California, Oakland, CA (US)

(72) Inventors: Lbachir BenMohamed, Irvine, CA (US); Anthony Nesburn, Malibu, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/493,070

(22) Filed: Sep. 22, 2014

(65) Prior Publication Data

US 2017/0065713 A1    Mar. 9, 2017

Related U.S. Application Data

(60) Provisional application No. 61/880,992, filed on Sep. 23, 2013.

(51) Int. Cl.
*A61K 39/245* (2006.01)
*C07K 14/035* (2006.01)
*C07K 14/005* (2006.01)
*A61K 39/00* (2006.01)

(52) U.S. Cl.
CPC .......... *A61K 39/245* (2013.01); *C07K 14/005* (2013.01); *A61K 2039/55561* (2013.01); *A61K 2039/57* (2013.01); *C12N 2710/16622* (2013.01); *C12N 2710/16634* (2013.01)

(58) Field of Classification Search
None
See application file for complete search history.

(56) References Cited

U.S. PATENT DOCUMENTS

| 6,015,565 | A  | * | 1/1999  | Rose ............... C07K 14/005 424/199.1 |
| 5,955,088 | A  | * | 9/1999  | Ghiasi ............. A61K 39/245 424/231.1 |
| 6,193,984 | B1 | * | 2/2001  | Ghiasi ............. A61K 39/245 424/231.1 |
| 2003/0219448 | A1 |   | 11/2003 | BenMohamed et al. |
| 2004/0197347 | A1 | * | 10/2004 | Sykes ............. A61K 39/245 424/186.1 |

OTHER PUBLICATIONS

Zhang et al., A genital tract peptide epitope vaccine targeting TLR-2 efficiently induces local and systemic CD8+ T cells and protects against herpes simplex virus type 2 challenge. Muc. Immunol., 2, 129-143, 2009.*
Gallichan et al., Specific secretory immune responses in the female genital tract following intranasal immunization with a recombinant adenovirus expressing glycoprotein B of herpes simplex virus. Vaccine, 13, 1589-1595, 1995.*
Hosken N.A., Development of a therapeutic vaccine for HSV-2. Vaccine, 23, 2395-2398, 2005.*
Bernstein et al., Herpes simplex vaccines. Vaccine, 17, 1681-1689, 1999.*
Kino et al., Immunogenicity of herpes simplex virus glycoprotein gB-1-related protein produced in yeast. Vaccine, 7, 155-160, 1989.*
Dervillez et al., Future of an 'asymptomatic' T-cell epitope-based therapeutic herpes simplex vaccine. Future Virol. 7, 371-378, 2012.*
Chentoufi et al., Mucosal Herpes Immunity and Immunopathology to Ocular and Genital Herpes Simplex Virus Infections. Clin. Dev. Immunol. Article ID 149135, 2012.*
Chentoufi et al., Towards a Rational Design of an Asymptomatic Clinical Herpes Vaccine: The Old, the New, and the Unknown. Clin. Dev. Immunol. Article ID 187585, 2012.*
Kalantari-Dehanghi et al. (Discovery of Potential Diagnostic and Vaccine Antigens in Herpes Simplex Virus 1 and 2 by Proteome-Wide Antibody Profiling. J Virol. 86, 4328-4339, 2012.*
Chentoufi et al., A Novel HLA (HLA-A0201) Transgenic Rabbit Model for Preclinical Evaluation of against Ocular Herpes Human CD8+ T Cell Epitope—Based Vaccines. J Immunol. 184, 2561-2571, 2010.*
Dasgupta et al., New concepts in herpes simplex virus vaccine development: notes from the battlefield. Expert Rev. Vaccines, 8, 1023-1035, 2009.*
Nesburn et al., Topical/Mucosal Delivery of Sub-Unit Vaccines That Stimulate the Ocular Mucosal Immune System. The Ocular Surface, 4, 178-187, 2006.*
Samandary, S., Kridane-Miledi, H., et al.; Associations of HLA-A, HLA-B and HLA-C alleles frequency with prevalence of herpes simplex virus infections and diseases across global populations; Hum Immunol, 75(8) 715-729; Aug. 2014.
Khan, A.A., Srivastava R., et al.; Asymptomatic memory CD8+ T cells: From development and regulation to consideration for human vaccines and immunotherapeutics; Human Vaccines & Immunotherapeutics; 10(4): 945-63. Feb. 2014.
Dervillez, X., Qureshi, H., et al.; Asymptomatic HLA-A*02:01-restricted epitopes from herpes simplex virus glycoprotein B preferentially recall polyfunctional CD8+ T cells from seropositive asymptomatic individuals and protect HLA transgenic mice against ocular herpes; J Immunol. 191(10): 5124-38; Nov. 2013.
Zhang, X., Dervillez, X., et al.; Targeting the genital tract mucosa with a lipopeptide/recombinant adenovirus prime/boost vaccine induces potent and long-lasting CD8+ T cell immunity against herpes: Importance of MyD88; J Immunol; 189(9): 4496-509; Nov. 2012.
Dasgupta, G., Benmohamed, L.; Of mice and not humans: how reliable are animal models for evaluation of herpes CD8(+)—T cell-epitopes-based immunotherapeutic vaccine candidates?; Vaccine, 29(35): 5824-36; Aug. 2011.
Chentoufi, A. et al.; The Herpes Simplex Virus 1 Latency-Associated Transcript Promotes Functional Exhaustion of Virus-Specific CD8+ T Cells in Latently Infected Trigeminal Ganglia: A Novel Immune Evasion Mechanism; Journal of Virology, 85(17): 9127-9138; Sep. 2011.

(Continued)

*Primary Examiner* — Elly-Gerald Stoica
(74) *Attorney, Agent, or Firm* — Archer Norris, PLC; Sean D. Senn; Priti D. Phukan

(57) ABSTRACT

Certain embodiments of the present invention provide immunogenic compositions that comprise one or more peptides having an amino acid sequence selected from the group consisting of NLLTTPKFT and RMLGDVMAV and methods for administering such compositions to a mammal and thereby inducing in the mammal a CD8+ T cell-dependent protective immunity against an HSV-1 infection, an HSV-2 infection, an HSV-1 condition, an HSV-2 condition, or combinations thereof.

11 Claims, 18 Drawing Sheets

(56) References Cited

OTHER PUBLICATIONS

Allen, S.J., et al.; The Role of LAT in Increased CD8+ T Cell Exhaustion in Trigeminal Ganglia of Mice Latently Infected with Herpes Simplex Virus 1; Journal of Virology, 85(9): 4184-4197; May 2011.

Chentoufi, A., et al.; A Novel HLA (HLA-A*0201) Transgenic Rabbit Model for Preclinical Evaluation of Human CD8 + T Cell Epitope-Based Vaccines against Ocular Herpes; J Immunol. 184(5): 2561-2571; Mar. 2010.

Mott, K., et al.; the Role of a Glycoprotein K (gK) CD8+ T-Cell Epitope of Herpes Simplex Virus on Virus Replication and Pathogenicity; Investigative Ophthalmology & Visual Science, 50(6): 2903-2912; Jun. 2009.

Mott, K., et al.; Level of Herpes Simplex Virus Type 1 Latency Correlates with Severity of Corneal Scarring and Exhaustion of CD8+ T Cells in Trigeminal Ganglia of Latently Infected Mice; Journal of Virology, 83(5): 2246-2254; Mar. 2009.

Chentoufi, A., et al.; HLA-A*0201-Restricted CD8+ Cytotoxic T Lymphocyte Epitopes Identified from Herpes Simplex Virus Glycoprotein D; Journal of Immunology, 180: 426-437; Oct. 2008.

Nesburn A., et al.; Functional Foxp3+ CD4+ CD25(Bright+) Natural Regulatory T Cells Are Abundant in Rabbit Conjunctiva and Suppress Virus-Specific CD4+ and CD8+ Effector T Cells during Ocular Herpes Infection; Journal of Virology, 81(14): 7647-7661; Jul. 2007.

Zhang, X., et al.; Th-Cytotoxic T-Lymphocyte Chimeric Epitopes Extended by Nε-Palmitoyl Lysines Induce Herpes Simplex Virus Type 1-Specific Effector CD8+ Tc1 Responses and Protect against Ocular Infection; Journal of Virology, 79(24): 15289-15301; Dec. 2005.

* cited by examiner

IMMUNOGENIC PEPTIDES FOR TREATMENT OF HERPES SIMPLEX VIRUS INFECTION AND CONDITIONS

PRIORITY DATA

The present application claims the benefit of U.S. Provisional Patent Application Ser. No. 61/880,990, which is hereby incorporated by reference in its entirety and which was filed Sep. 23, 2013.

This invention was made in part with United States Government support under Public Health Service Research Grants EY14900 and EY019896 from the National Institutes of Health.

FIELD OF THE INVENTIONS

Embodiments of the inventions relate to immunogenic peptide sequences of Herpes Simplex Virus type 1 (HSV-1) and/or Herpes Simplex Virus type 2 (HSV-2) glycoprotein B (gB) useful in the inhibition and/or treatment of HSV infection and/or conditions.

BACKGROUND OF THE INVENTIONS

The incidence of HSV has risen 30 percent since the 1970s. One in four adults is infected with HSV, and there are an estimated one million new cases of HSV infection every year. There are two forms of herpes, commonly known as HSV-1 and HSV-2. Although HSV-1 is frequently associated with cold sores and HSV-2 with genital herpes, the viruses have many similarities and can infect either area of the body. There is a high degree of homology between the sequence of HSV-1 and HSV-2, the overall incidence of identical aligned nucleotides being superior to 80% in protein-coding regions.

Individuals that carry HSV-1 and/or HSV-2 can be symptomatic (SYMP) and suffer a wide range of HSV conditions (e.g., cold sore, ocular lesion, corneal blindness, encephalitis, cervical cancer, throat infections, rash, meningitis, nerve damage, and genital herpes) on a recurrent basis throughout their lives. Many HSV-infected individuals are asymptomatic (ASYMP), yet frequently and spontaneously shed reactivated virus in their body fluids (e.g., saliva, tears, and vaginal secretions). The percentage of HSV-infected individuals who are not cognizant of their own infection is over 50%, largely because these individuals either do not experience any HSV conditions or because they dismiss HSV conditions as merely annoying itch, rash, cold sore, etc. HSV may be treated in a palliative manner with, e.g., acyclovir and related compounds, but there is no cure for HSV infection. Therefore, individuals cannot rid themselves of of HSV once infected. Accordingly, clinically effective treatments for the inhibition of HSV infection and/or amelioration of HSV conditions are needed.

SUMMARY OF THE INVENTIONS

Embodiments of the present invention provide isolated immunogenic peptides that have an amino acid sequence at least 60% identical, at 70% identical, at least 80% identical, at least 90% identical, or 100% identical to an amino acid sequence selected from the group consisting of NLLTTPKFT and RMLGDVMAV. In some embodiments, such peptides are formulated in immunogenic compositions capable of inducing in a mammal a CD8+ T cell-dependent protective immunity against an HSV-1 infection, an HSV-2 infection, an HSV-1 condition, an HSV-2 condition, or combinations thereof. In some embodiments, such immunogenic compositions further comprise an adjuvant selected from the group consisting of CpG1826 and lipid-tailed peptides (i.e. lipopeptides). In some embodiments, such compositions further comprise peptides that contain an epitope selected from the group consisting of PADRE and epitopes from HSV-1 gB, gD or any of its 84+ proteins.

Embodiments of the present invention provide methods of inducing in a mammal a CD8+ T cell-dependent protective immunity against an HSV-1 infection, HSV-2 infection, an HSV-1 condition, an HSV-2 condition, or combinations thereof. Such methods involve the step of administering to a mammal an immunogenic composition that comprises peptides that have an amino acid sequence at least 60% identical, at 70% identical, at least 80% identical, at least 90% identical, or 100% identical to an amino acid sequence selected from the group consisting of NLLTTPKFT and RMLGDVMAV.

BRIEF DESCRIPTION OF THE DRAWINGS

FIG. 1A shows FACS data plots of the frequencies of $CD8^+$ T cells detected in PBMCs of an HSV-1 seropositive individual following a 5-day expansion with the indicated gB epitope peptides, determined as described in Example 9. FIG. 1B is a plot of the percentage of $CD8^+$ T cells detected in PBMCs from 10 HLA-A*02:01positive, HSV-1 seropositive individuals and 10 HLA-A*02:01positive, HSV-1 seronegative individuals that recognize the indicated gB epitope peptides. FIG. 1C is a plot of gB epitope peptide-specific, IFN-γ-producing $CD8^+$ T cells detected in PBMCs of $HSV^+$ or $HSV^-$, HLA-A*02:01positive individuals stimulated with the indicated gB epitope peptides, determined as described in Example 11. In FIG. 1C, spot forming cells=mean number of spots in the presence of antigen (Ag)–mean number of spots in the absence of stimulation. FIG. 1D shows plots of $CD8^+$ T cell proliferation in the presence of 10 μof the indicated gB epitope peptides detected in PBMCs of $HSV^+$ individuals, determined as described in Example 8. FIG. 1E is a plot of the absolute numbers of dividing $CD8^+$ T cells per 300,000 total cells after 5 day stimulation.

FIG. 5A is a plot of the clinical scores of SYMP, ASYMP, and MOCK group mice. FIG. 5B is a plot of mean HSV-1 titres of SYMP, ASYMP, and MOCK group mice. FIG. 5C is a plot of the percent survival of SYMP, ASYMP, and MOCK group mice. FIG. 5D is a scattergram plot and linear regression analysis of mouse survival (%) and HSV-specific CD8$^+$ T cell responses after challenge with HSV-1. Correlation was performed using the Pearson test with two-tailed p value analysis ($r^2$ =0.7996; p<0.0001). FIG. 5E is a plot of the percent survival of ASYMP CD8$^+$ T cell epitope peptide immunized mice following ocular herpes challenge and depletion of CD8$^+$ T cells or CD4$^-$ T cells. by i.p. injection with six doses (1 every other day) of 100 μl saline containing anti-CD4, anti-CD8, or isotype control.

DETAILED DESCRIPTION OF THE INVENTIONS

Figure 1A:
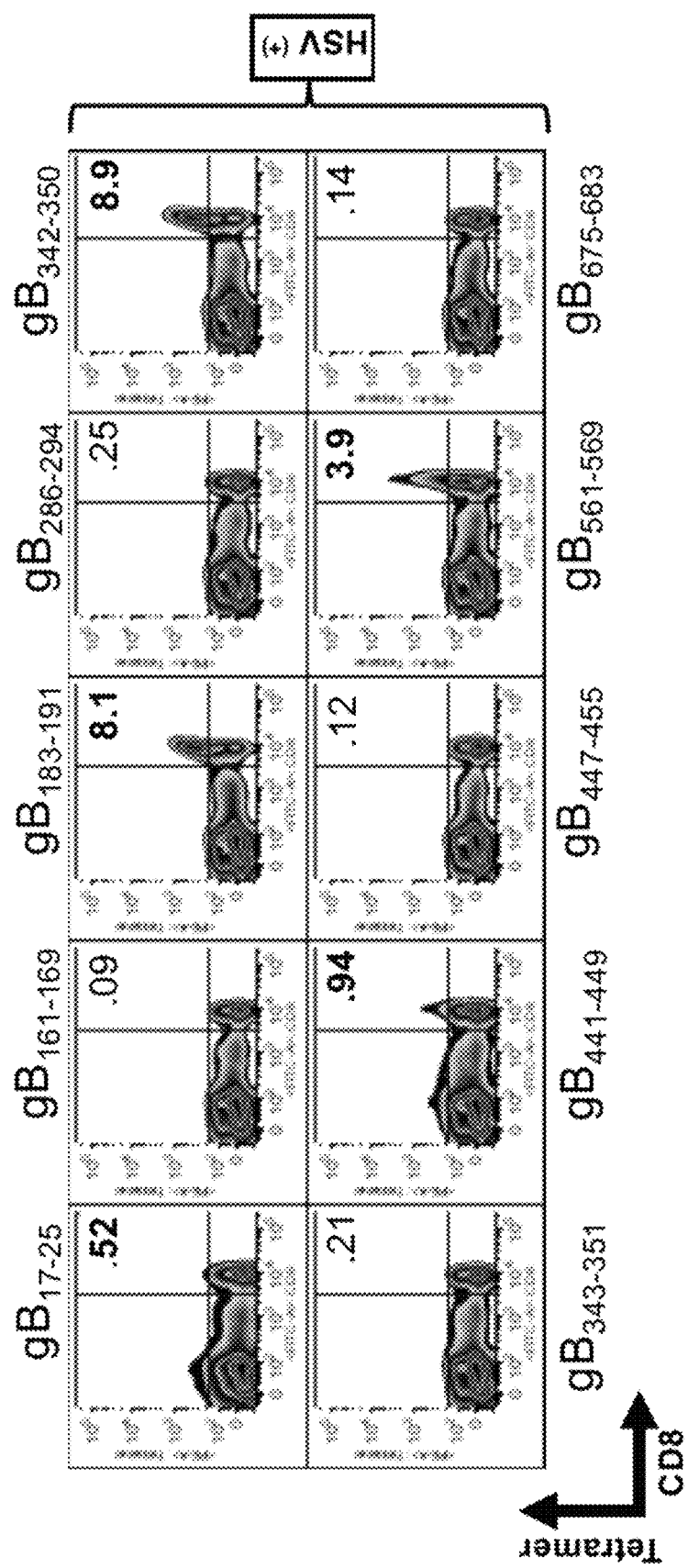
FIGS. 1A-1E report experimental results of peripheral blood mononuclear cell (PBMC) derived $CD8^+$ T cells analyzed ex vivo after in vitro expansion.
Figure 1B:
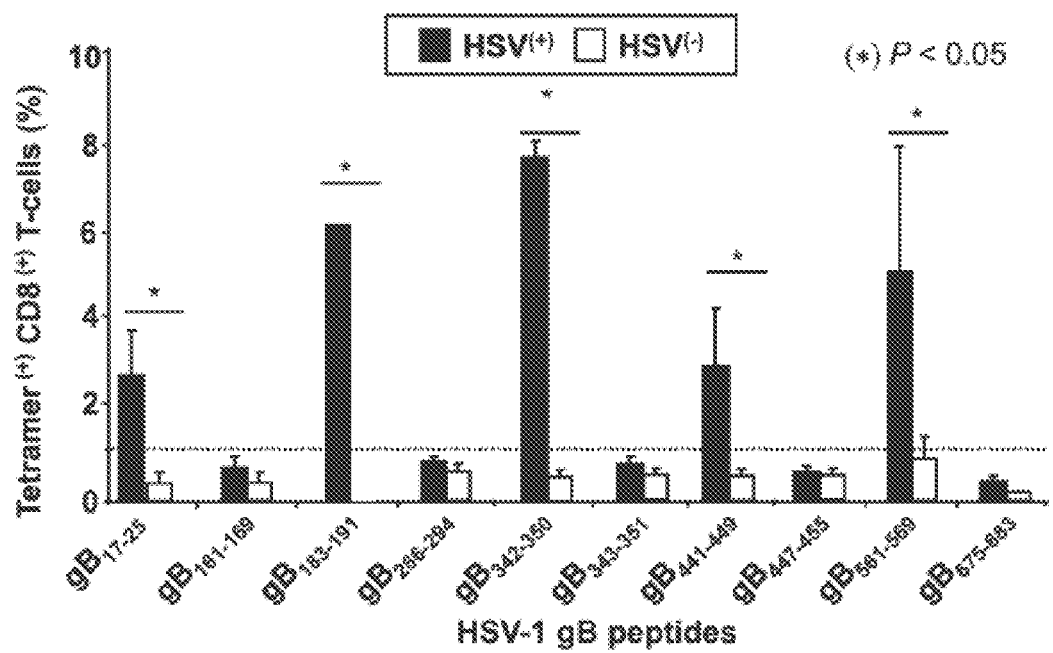
Figure 1C:
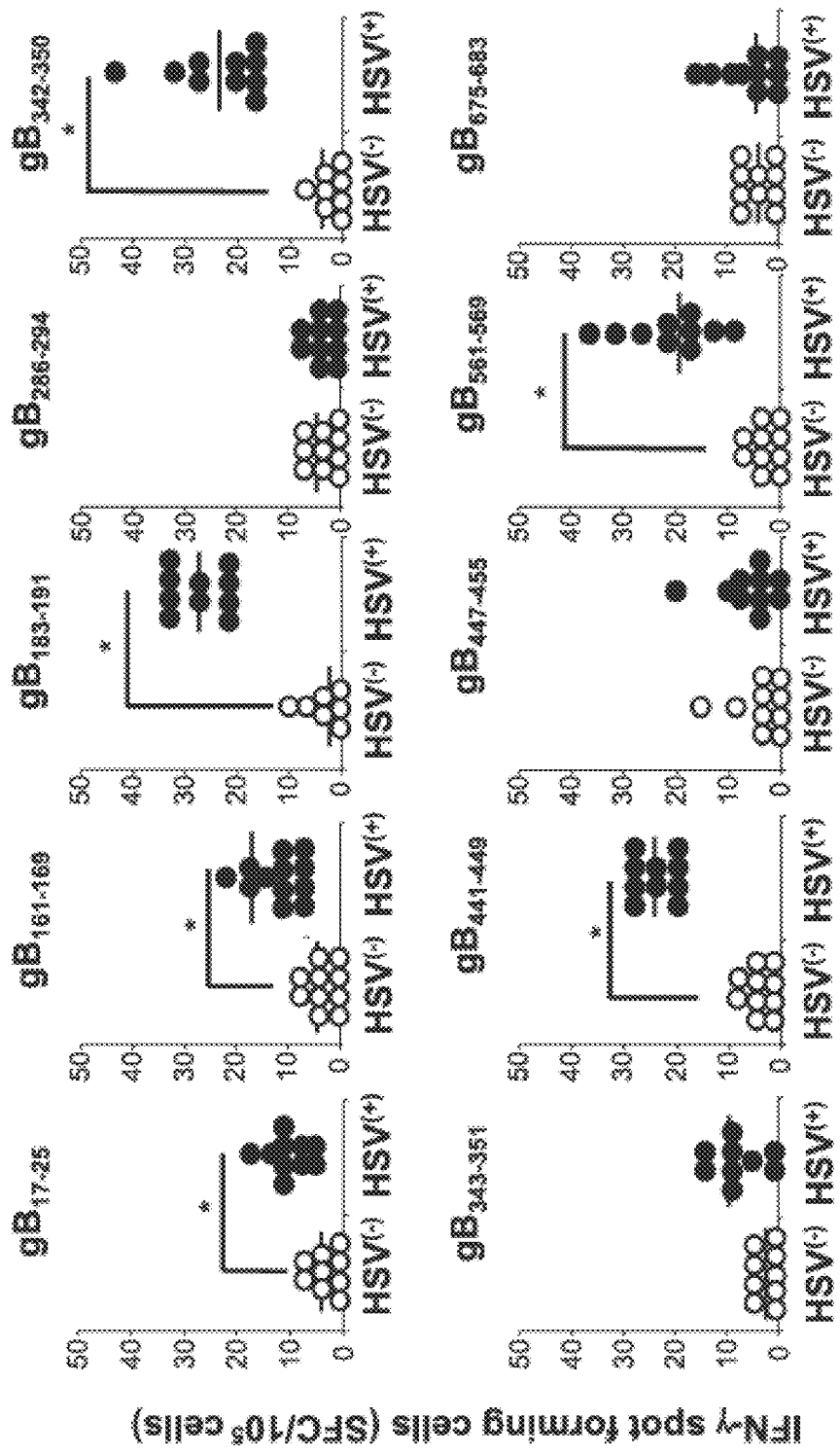
Figure 1D:
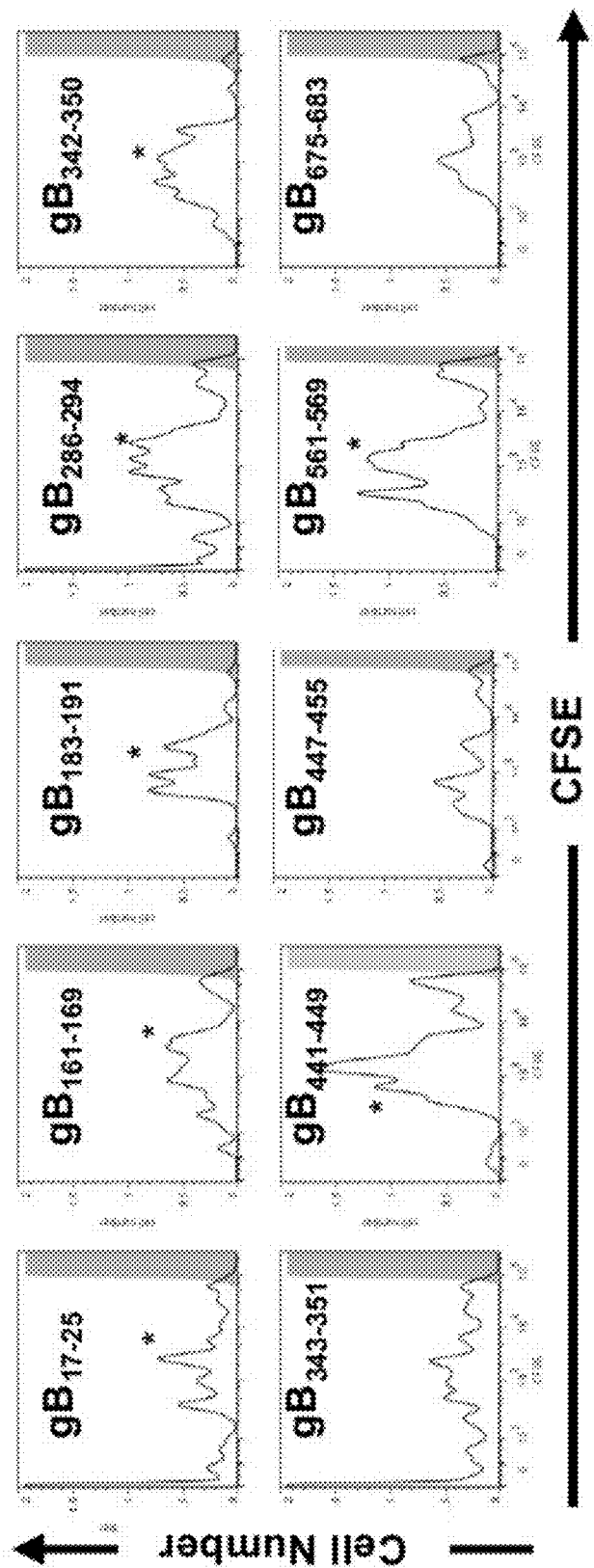
Figure 1E:
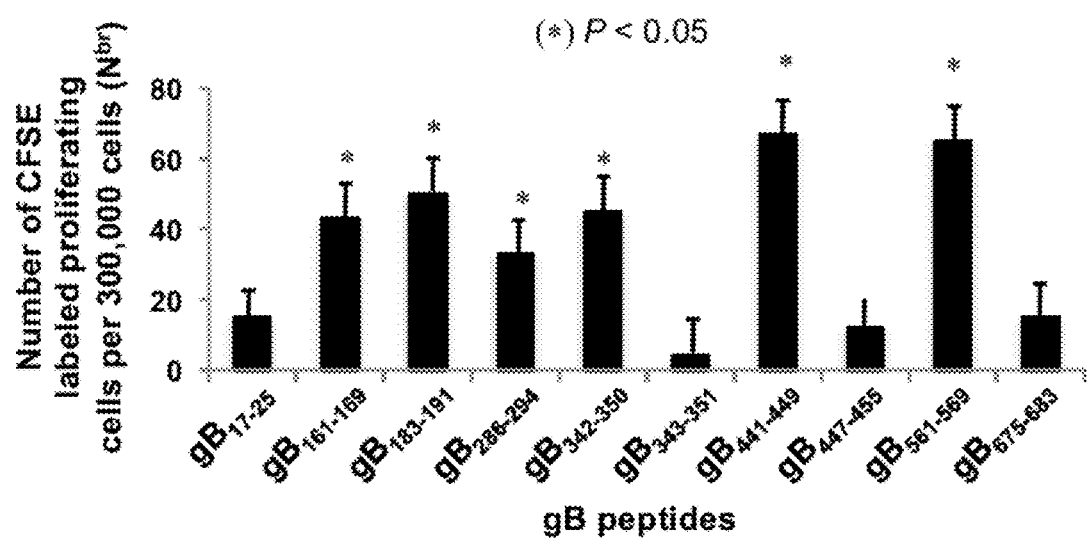

We compared the population size, specificity, and function of HLA-restricted, HSV-1 gB specific CD8$^+$ T cells from ASYMP and SYMP individuals; and significant quantitative and qualitative differences were found between such CD8$^+$ T cells. Two HSV-1 gB epitopes were identified that CD8$^+$ T cells from ASYMP individuals preferentially recognized: i.e., gB$_{342-350}$ and gB$_{561-569}$. Immunization of humanized, HLA-transgenic mice with these ASYMP epitopes resulted in significant inhibition of HSV infection and conditions. Two HSV-1 gB epitopes were identified that CD8$^+$ T cells from SYMP individuals preferentially recognized: i.e., gB$_{183-191}$ and gB$_{441-449}$. Immunization of humanized, HLA-transgenic mice with these SYMP epitopes resulted in little inhibition of HSV infection and conditions.

In silico Prediction of Potential HLA-A*02:01Restricted T Cell Epitopes from HSV-1 gB Ag. The HSV-1 (strain 17) gB amino acid sequence was searched for potential HLA-A*02:01 binding regions using BIMAS, SYFPEITHI, and MAPPP predictive computational algorithms. These searches identified the 10 epitopes reported in Table I as having a high predicted affinity to the HLA-A*02:01 molecule, a haplotype represented in >50% of the world human population. The 10 predicted epitopes were therefore selected for experimental evaluation.

TABLE 1

| Peptide | Sequence | Molecular Mass (kDa) | Amino Acids (No.) | BIMAS | SYFPEITHI | MAPPP | MHCPred |
|---|---|---|---|---|---|---|---|
| gB$_{17-25}$ | ALLGLTLGV SEQ ID NO: 1 | 856.0 | 9 | 257.342 | 31 | 0.5241 | 0.27 |
| gB$_{161-169}$ | TMYYKDVTV SEQ ID NO: 2 | 1119.3 | 9 | 160.742 | 23 | 0.8421 | 0.34 |
| gB$_{183-191}$ | GIFEDRAPV SEQ ID NO: 3 | 1003.1 | 9 | 145.077 | 24 | 0.5003 | 0.24 |
| gB$_{286-294}$ | FVLATGDFV (SEQ ID NO: 4 | 968.1 | 9 | 279.149 | 17 | — | 0.09 |
| gB$_{342-350}$ | NLLTTPKFT SEQ ID NO: 5 | 1034.2 | 9 | 151.648 | 15 | — | — |
| gB$_{343-351}$ | LLTTPKFTV SEQ ID NO: 6 | 1019.2 | 9 | 685.783 | 24 | 1 | 0.19 |
| gB$_{441-449}$ | YLANGGFLI SEQ ID NO: 7 | 967.1 | 9 | 278.347 | 24 | — | 0.2 |
| gB$_{447-455}$ | FLIAYQPLL SEQ ID NO: 8 | 1077.3 | 9 | 98.267 | 25 | 0.8300 | 0.4 |
| gB$_{561-569}$ | RMLGDVMAV SEQ ID NO: 9 | 991.2 | 9 | 427.474 | 27 | 0.7222 | 0.37 |
| gB$_{675-683}$ | TMLEDHEFV SEQ ID NO: 10 | 1120.2 | 9 | 2053.642 | 22 | 0.9942 | 0.19 |

The numbers in the four right columns of Table I show predicted IC$_{50}$ as calculated by BIMAS, SYFPEITHI, MAPPP, and MHCPred.

Nine of the 10 selected gB epitopes shared the HLA-A*02:01 binding motifs: leucine, isoleucine, or methionine at the second position and valine, leucine, isoleucine, or threonine at the ninth position. As indicated by MHCPred computational algorithm, all 10 gB sequences carrying predicted antigenic and immunogenic HLA-A*02:01binding CD8+ T cell epitopes were more susceptible to proteolysis, an event that precedes T cell epitope presentation in association with HLA molecules (data not shown).

The 10 predicted epitopes were not confined to a particular region of gB. One of the 10 predicted epitopes, $gB_{17-25}$, localized to the gB signal sequence. Seven localized to the external N-terminal ectodomain portion of gB (i.e., $gB_{161-169}$, $gB_{183-191}$, $gB_{286-294}$, $gB_{342-350}$, $gB_{343-351}$, $gB_{441-449}$, and $gB_{447-455}$). Two localized adjacent to the hydrophobic membrane transmembrane anchor domain ($gB_{561-569}$ and $gB_{675-683}$) None of the 10 predicted epitopes is localized to the transmembrane or the C-terminal intracellular domain of gB and none localized to known glycosylated regions of gB.

Figure 2A:
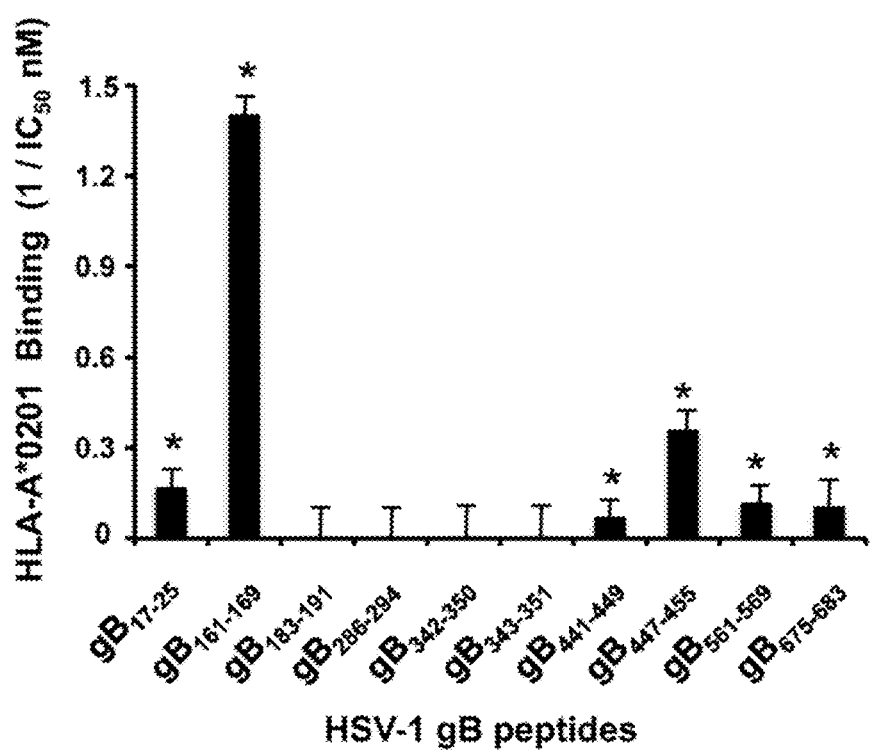
FIG. 2A is a plot of HLA-A*0201 in vitro binding affinities for the indicated gB epitope peptides to soluble HLA-A*0201 molecules, determined as described in Example 4. A reference non-herpes peptide was used to validate each assay. Data are expressed as relative activity (ratio of the $IC_{50}$ of the test peptide to the $IC_{50}$ of the reference peptide).

Six of the 10 Predicted gB Epitope Peptides Bind with High Affinity to HLA-A*02:01 and Stabilize its Expression on the Surface of Target Cells. Peptides corresponding to the 10 predicted epitopes were synthesized as described in Example 3, and the binding affinity of each peptide to HLA-A*02:01 molecules was determined as described in Example 4. FIG. 2A reports the results of these binding affinity assays. As can be seen in FIG. 2A, six of the predicted epitopes (i.e., $g_{17-25}$, $gB_{161-169}$, $gB_{441-449}$, $gB_{447-455}$, $gB_{561-569}$, and $gB_{675-683}$) bound with high affinity (Kd<100 nM) to HLA-A*02:01 molecules. Two of the predicted epitopes (i.e., $gB_{286-294}$ and $gB_{343-351}$) bound to HLA-A*02:01 with intermediate affinity (Kd between 100 nM and 500 nM). And two of the predicted epitopes (i.e., $gB_{183-191}$ and $gB_{342-350}$) bound to HLA-A*02:01 with low binding affinities (Kd>500 nM).

Figure 2B:
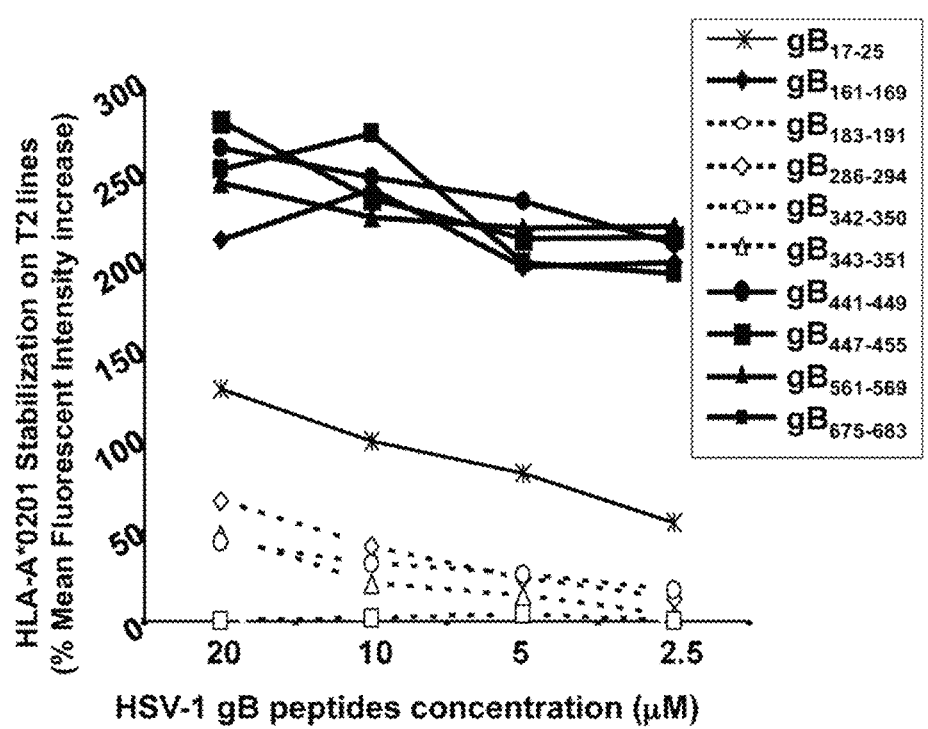
FIG. 2B is a plot of stabilization of HLA-A*02:01 molecules on the surface of T2 cells by the indicated gB epitope peptides, determined as described in Example 5.

Peptides corresponding to the 10 predicted gB epitopes were used to perform a stabilization assay of HLA-A*02:01 molecules on the cell membrane of $T_2$ cells as described in Example 5. This assay used a monoclonal antibody (mAb) specific to a folded structure of HLA-A*02:01 to estimate in a FACS assay the relative amount of HLA-A*02:01 molecules retained on the surface of T2 cells following incubation with a predicted gB peptide epitope. The amount of empty HLA-A*02:01 molecules retained on the surface of $T_2$ cells is normally at a low level. Each predicted gB epitope peptide was tested individually at four descending concentrations: 20 μM, 10 μM, 5 μM, and 2.5 μM, As shown in FIG. 2B, 5 of 10 peptides (i.e., $gB_{161-169}$, $gB_{441-449}$, $g_{B447-455}$, $gB_{561-569}$, and $gB_{675-683}$) significantly increased the level of HLA-A*02:01 molecules detectable by FACS on the surface of T2 cells in a dose-dependent manner, indicating a high affinity of those peptides to HLA-A*02:01 molecules (p<0.005). The $gB_{17-25}$ peptide demonstrated a moderate stabilization ability of HLA-A*02:01 molecules on the surface of T2 cells, indicating a medium affinity of this peptide for HLA-A*02:01 molecules. The remaining four peptides produced no significant stabilization of HLA-A*02:01 molecules on the surface of T2 cells.

The predicted gB epitope peptides shown in FIG. 2A to have high HLA-A*02:01 binding affinity also stabilized HLA-A*02:01 molecules on the cell surface of T2 cells, as shown in FIG. 2B. Taken together, these results indicate that the $gB_{17-25}$, $gB_{161-169}$, $gB_{441-449}$, $gB_{447-455}$, $gB_{561-569}$, and $gB_{675-683}$ peptides bind HLA-A*02:01 with high affinity and stabilize HLA-A*02:01 on the surface of target cells.

Frequent IFN-γ-Producing CD8+ T Cells, Specific to $gB_{17-25}$, $gB_{183-191}$, $gB_{342-350}$, $gB_{441-449}$, and $gB_{561-569}$, Detected in HLA-A*02:01-Positive, HSV-Seropositive Individuals. CD8+ T cell responses specific to each predicted gB epitope peptide were studied in HLA-A*02:01positive, HSV-seropositive individuals. HLA-A*02:01positive, HSV-seronegative individuals were used as controls. The characteristics of the study population with respect to gender, age, HSV-1 and HSV-2 seropositivity, and HLA-A*02:01 frequency distribution are described in Example 1. This study focused solely on individuals who are HSV-1 seropositive and HSV-2-seronegative.

Figure 3A:
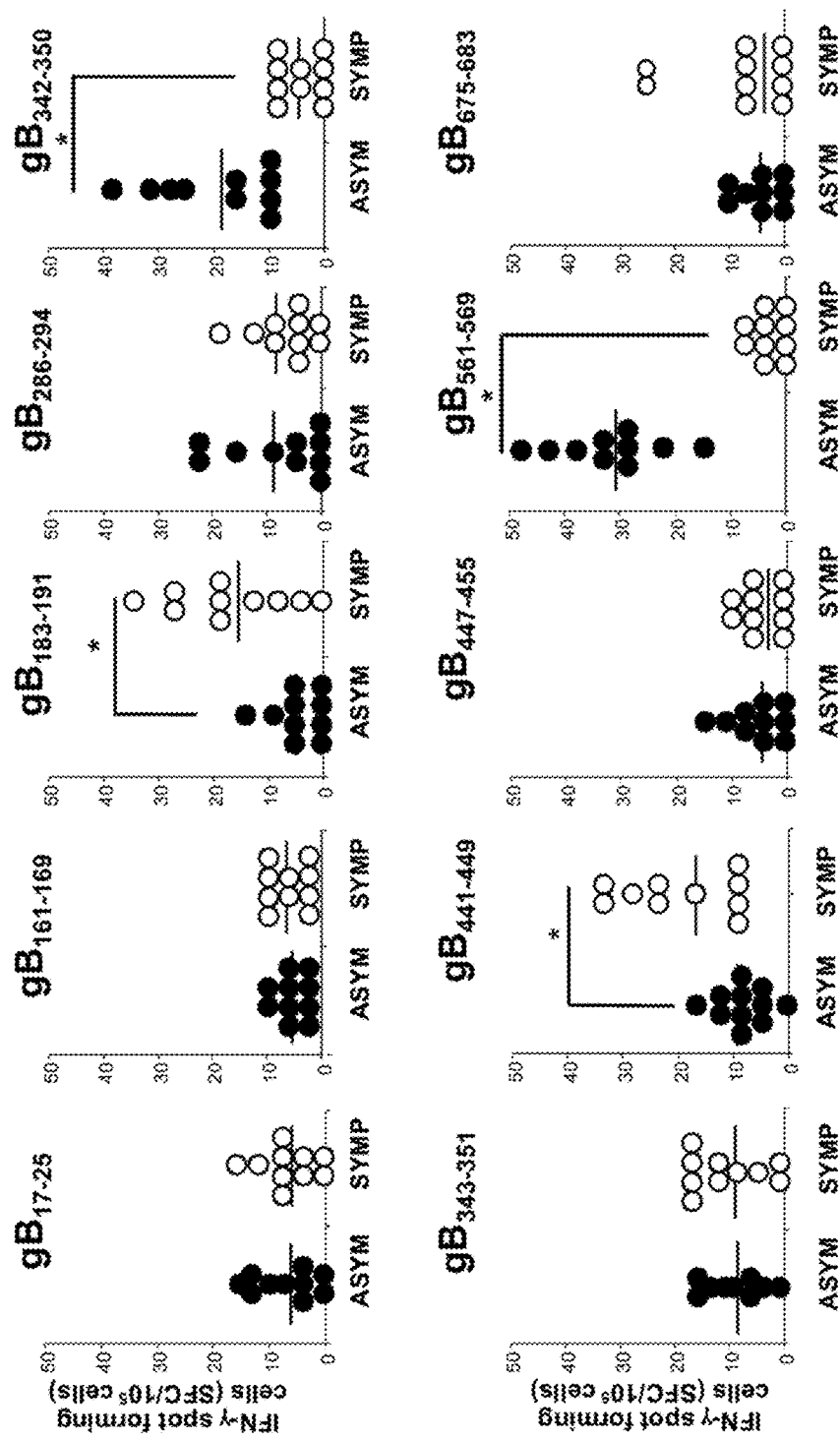
FIG. 3A shows plots of IFN-γ spot forming $CD8^+$ T cells detected in PBMCs of 10 ASYMP and 10 SYMP individuals, stimulated with indicated gB epitope peptides. The number of gB epitope peptide-specific, IFN-γ-producing T cells was determined by ELISPOT assay, as described in Example 11.
Figure 3B:
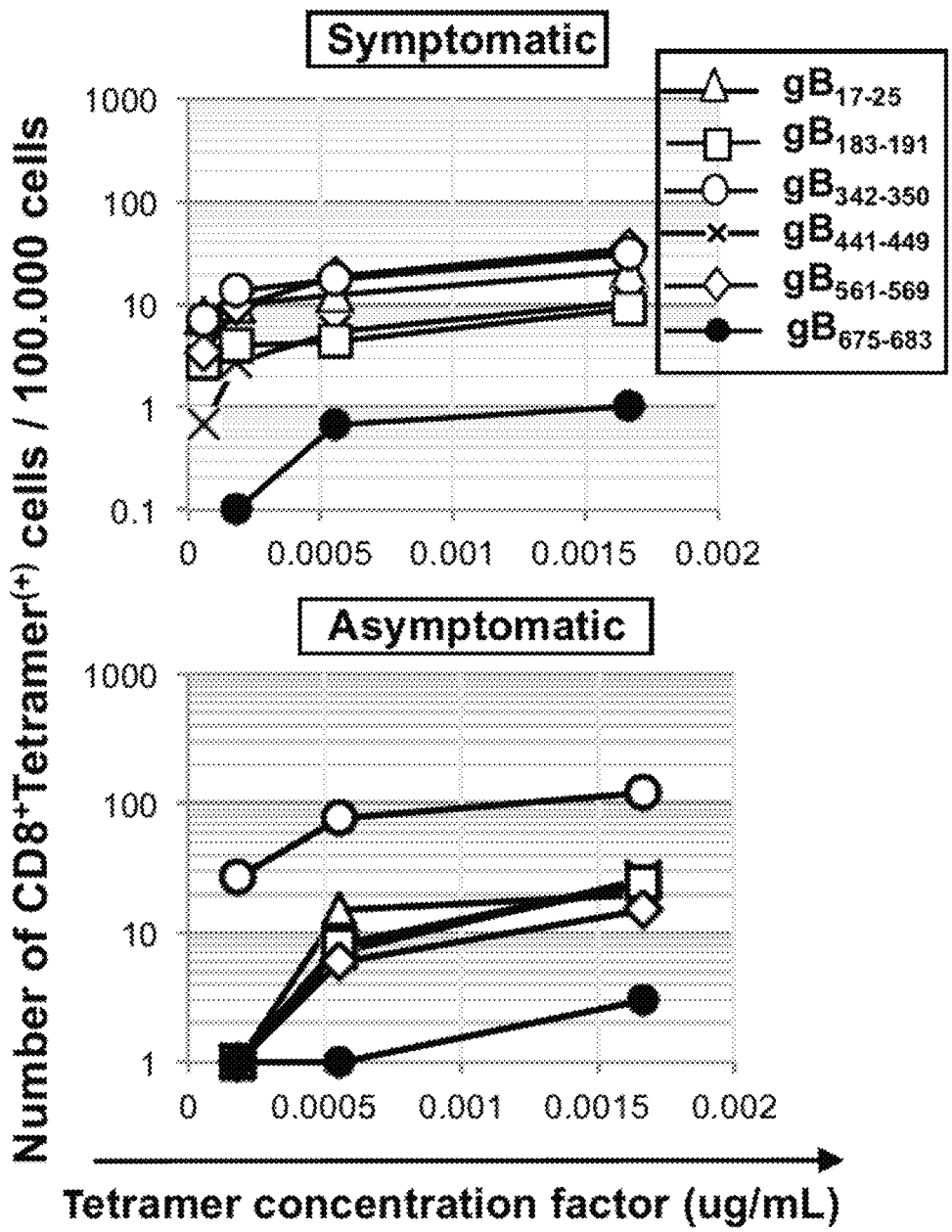
FIG. 3B shows plots of the number of $CD8^+$ tetramer+ cells detected in PBMCs of one SYMP individual and one ASYMP individual as a function of tetramer concentration for the indicated gB epitope peptides.

The frequency of CD8+ T cells specific to each of the 10 gB predicted epitope peptides was first determined in PBMCs isolated as described in Example 7 from HSV-1 seropositive individuals using peptide/PE-labeled HLA-A*02:01 tetramers, together with FITC-conjugated mAb specific to human CD8+ T cells (FIG. 3A and Example 10). After peptide in vitro stimulation, significantly higher percentages of tetramer+ CD8+ T cells specific to 5 of the 10 predicted epitope peptides ($gB_{17-25}$, $gB_{183-191}$, $gB_{342-350}$, $gB_{441-449}$, and $gB_{561-569}$) were detected in PBMCs of 10 HLA-A*02:01-positive, HSV-1 seropositive individuals compared to PBMCs of 10 HLA-A*02:01-positive, HSV-1 seronegative individuals (p<0.005; FIG. 3A and FIG. 3B). The highest frequencies of tetramer+ CD8+ T cells, detected with or without in vitro expansion, were recorded against $gB_{183-191}$, $gB_{342-350}$, and $gB_{561-569}$ peptide epitopes (5.5-8.9%).

CD8+ T cells, isolated from fresh peripheral blood in each group, were stimulated for 5 days with individual gB predicted epitope peptides and the number of gB-epitope-specific, IFN-γ-producing CD8+ T cells was determined in a 24-hour ELISPOT assay described in Example 11. As shown in FIG. 3A, 2 of 10 peptides, $gB_{342-350}$ and $gB_{561-569}$, induced significantly higher IFN-γ-producing CD8+ T cells from 10 sequentially studied HLA-A*02:01-positive, HSV-1 seropositive ASYMP healthy individuals as compared with 10 SYMP individuals, indicating that those two epitopes are ASYMP epitopes (p<0.005). In contrast, $gB_{183-191}$ and $gB_{441-449}$ peptides induced significantly higher IFN-γ-producing CD8+ T cells preferentially from SYMP individuals compared with ASYMP individuals, indicating that those two epitopes are SYMP epitopes (p<0.005). The $gB_{17-25}$ and $gB_{286-294}$ peptides induced significantly higher IFN-γ-producing CD8+ T cells in both SYMP and ASYMP individuals.

Figure 3C:
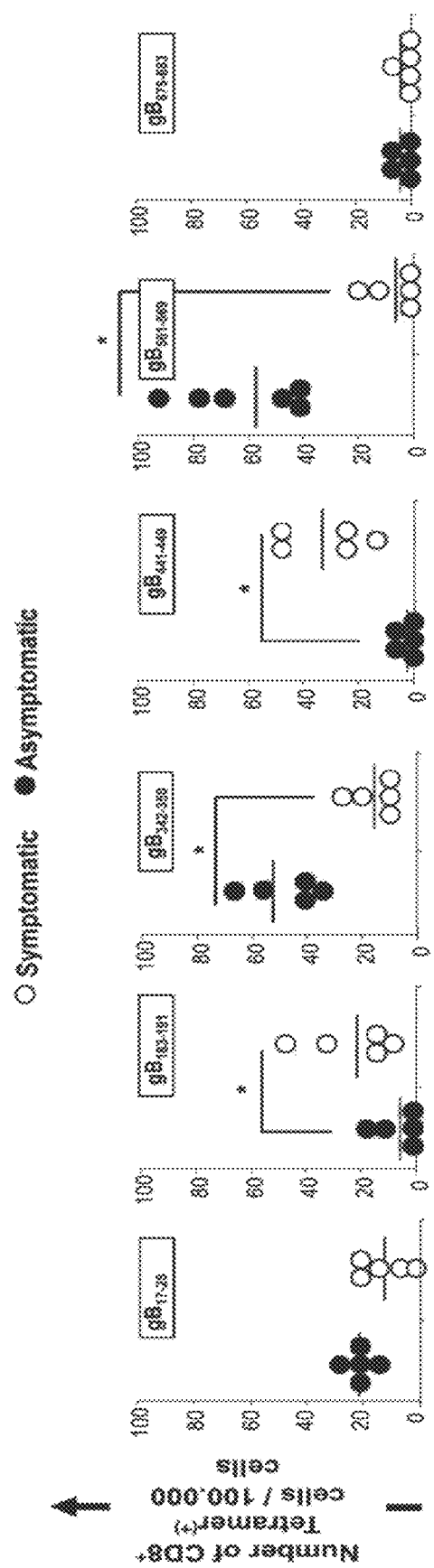
FIG. 3C shows plots of the average number of indicated gB epitope peptide-specific, $CD8^+$ T cells detected in PBMCs of five HLA-A*02:01positive, HSV-1 seropositive SYMP individuals and five ASYMP individuals.
Figure 5A:
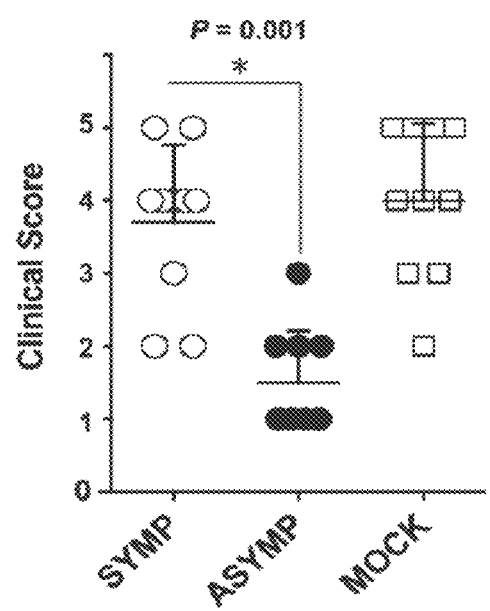
FIGS. 5A-5E show data from experiments described in Examples 14-17 of CD8$^+$ T cell dependent protective immunity against ocular herpes induced by ASYMP epitope peptides in humanized HLA transgenic mice.
Figure 5B:
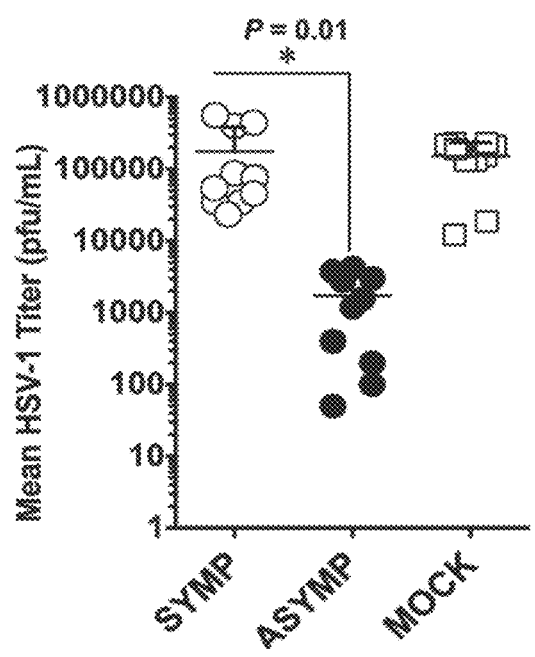
Figure 5C:
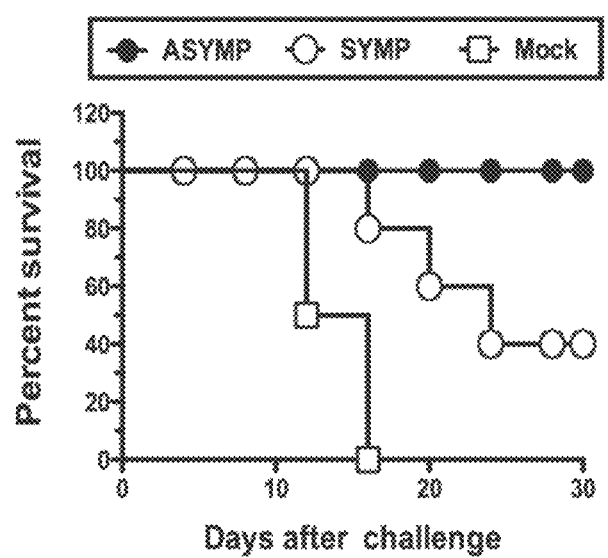

The analysis was then extended to assess the frequency of circulating CD8+ T cells, specific to each of the five, immunodominant gB epitopes ($gB_{17-25}$, $gB_{183-191}$, $gB_{342-350}$, $gB_{441-449}$, and $gB_{561-569}$), in PBMCs isolated from five ASYMP and five SYMP individuals. The subdominant epitope $gB_{675-683}$ was used as control. To obtain an objective enumeration of gB epitope-specific CD8+ T cells, each tetramer was tested at three or four dilutions and the numbers (instead of percentage) of epitope-specific CD8+ T cells per 100,000 T cells were determined. Significantly more tetramer+ CD8+ T cells specific to $gB_{342-350}$ and $gB_{561-569}$ epitopes were detected in ASYMP individuals, confirming these as ASYMP epitopes (p<0.005; FIG. 3B, FIG. 3C). In contrast, significantly higher numbers of tetramer+ CD8+ T cells specific to $gB_{383-191}$ and $gB_{441-449}$ epitopes were detected in SYMP individuals (p<0.005; FIG. 3B, and FIG. 5C), indicating these as SYMP epitopes.

Asymptomatic gB Epitope Specific CD8+ T Cells Displayed Concurrent Polyfunctional Activities and Recognized Naturally Processed Epitopes on HSV-1-Infected Target Cells. The cytotoxic function of CD8+ T cells from SYMP and ASYMP individuals were examined. CD107a and CD107b are lysosomal associated membrane glycoproteins that surround the core of lytic granules in cytotoxic T cells (CTLs). Upon TCR engagement and stimulation by antigens in association with MHC molecules, CD107a/b are exposed on the cell membranes of cytotoxic T cells. Accordingly, the level of CD107a/b expression on the surface of CTLs is used as a direct assay for the epitope-specific CTL response.

To assess whether gB epitope peptide-specific CD8+ T cells display CTL activity, fresh PBMC-derived CD8+ T cell lines were generated from HLA-A*02:01positive ASYMP and HLA-A*02:01positive SYMP individuals following stimulation in vitro with individual ASYMP (gB342-350 and gB561-569) or SYMP (gB183-191 and gB441-449) peptides as described in Example 13. The cytotoxicity of each of the four CD8+ T cell lines was measured against autologous target monocyte-derived dendritic cells either uninfected (mock) or infected with UV-inactivated HSV-1, with a vaccinia virus expressing gB (VVgB), or with a control vaccinia virus expressing glycoprotein D (VVgD) by detecting the level of CD107a/b expression by FACS on gated CD8+ T cells.

A high percentage of ASYMP g $B_{342\text{-}350}$ and $gB_{561\text{-}569}$ epitope-specific CD8+ T cells from healthy HLA-A*02:01positive, HSV-seropositive ASYMP individuals expressed significant levels of CD107a/b (percentage of CD107a/b/CD8+ T cells) following incubation with either HSV-1infected or VVgB-infected target monocyte-derived dendritic cells. In contrast, very few SYMP $gB_{183\text{-}191}$ and $gB_{441\text{-}449}$ epitope-specific CD8+ T cells upregulated CD107a/b after incubation with HSV-1infected or VVgB-infected target cells. No significant percentage of SYMP or ASYMP epitope peptide-specific CD8+ T cells upregulated CD107a/b after incubation with mock-infected or VVgD-infected target cells. These results indicate that ASYMP epitope-induced CD8+ T cells have cytotoxic activity against HSV-1infected cells and are able to specifically recognize endogenously processed gB epitopes from both HSV-1-infected and VVgB-infected target cells. There was no CTL response against any peptides in individuals that were seronegative for HSV, regardless of whether they were HLA-A*02:01positive or HLA-A*02:01negative (data not shown).

Figure 4A:
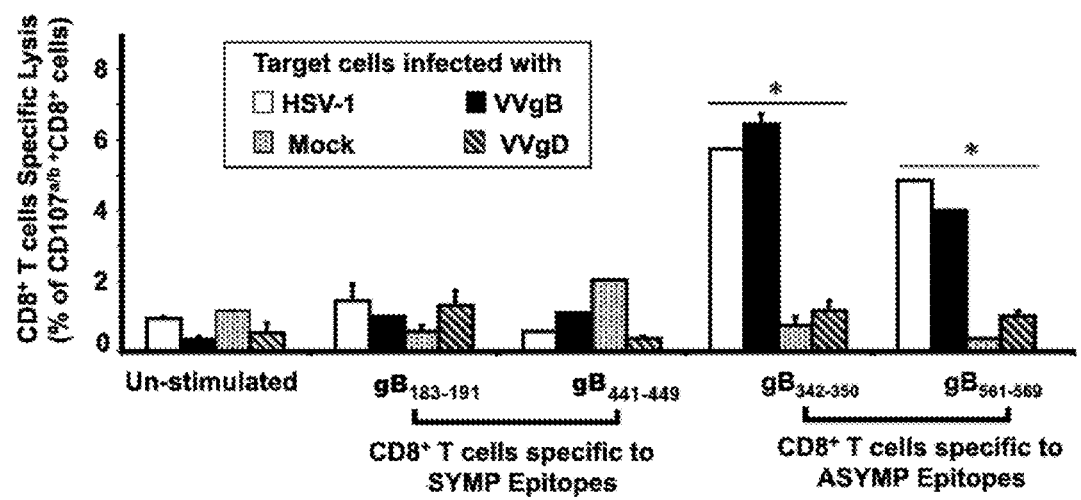
FIG. 4A is a plot of the percentage of CD107$^{a/b+}$ CD8$^+$ T cells specific to gB$_{342-350}$, gB$_{561-569}$, gB$_{183-191}$, and gB$_{441-449}$ epitope peptides from HLA-A*02:01positive ASYMP (n=5) or SYMP (n=5) individuals incubated with autologous, monocyte-derived dendritic cells (moDCs) infected with HSV-1, VVgB, VVgD, or mock infected as a function of being stimulated with the indicated SYMP or ASYMP epitope peptides or being unstimulated, determined as described in Example 13.
Figure 4B:
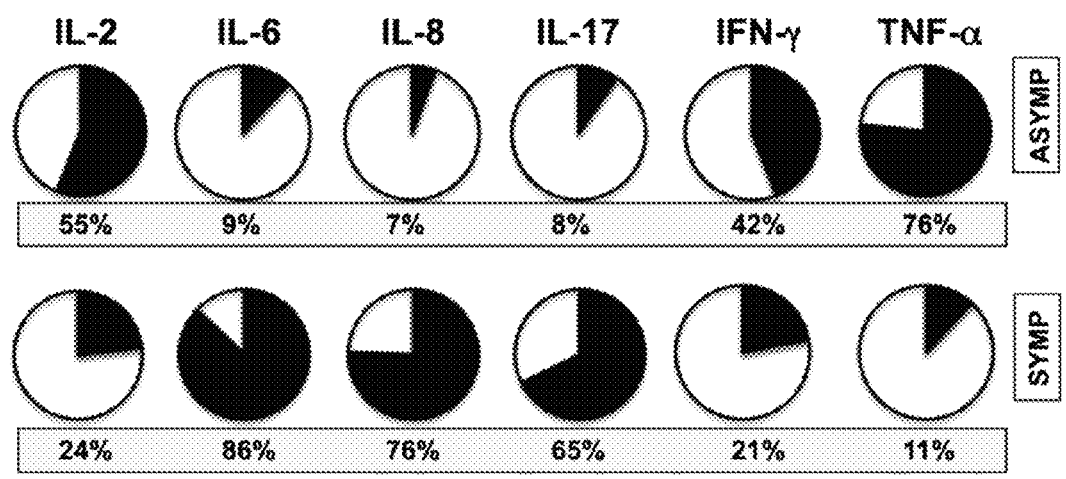
FIG. 4B shows pie charts of the average amounts of indicated cytokines produced by CD8$^+$ T cells from ASYMP patients (n=10, top row) and SYMP patients (n=8, bottom row) determined as described in Example 12. The average percentage of indicated cytokine-producing CD8$^+$ T cells is shown under each pie chart.

The levels of six inflammatory cytokines (IL-2, IL-6, IL-8, IL-17, IFN-γ, and TNF-a) produced by CD8+ T cells from ASYMP versus SYMP individuals following in vitro restimulation with UV-inactivated HSV-1 (strain McKrae) were compared by the Luminex microbeads system. As shown in FIG. 4B, CD8+ T cells from SYMP patients produced high levels of IL-6, IL-8, and IL-17 (black-filled portion of the pie chart), consistent with differentiated inflammatory T cells. In contrast, T cells from ASYMP individuals produced more of the effector cytokines IL-2, IFN-γ, and TNF-α (black-filled portion of the pie chart).

Figure 4C:
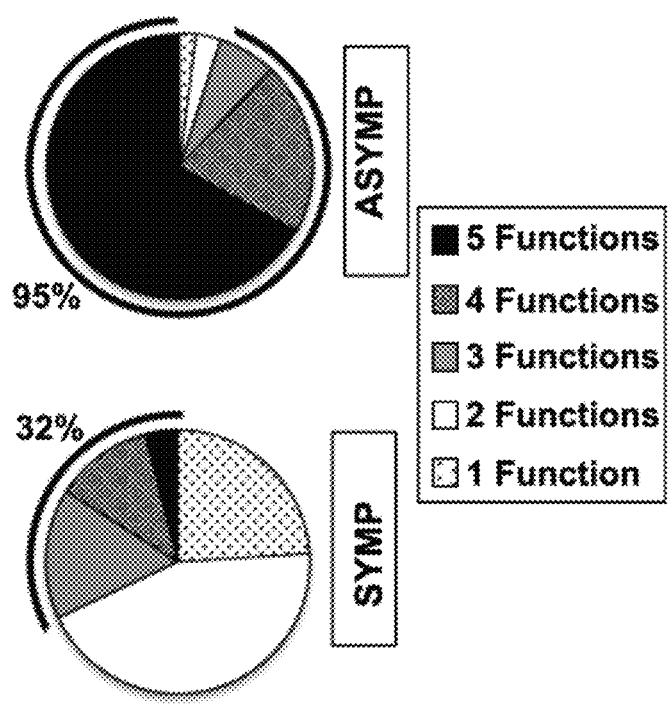
FIG. 4C shows pie charts of the overall mean of CD8$^+$ T cell functions from five HLA-A*02:01positive ASYMP and five SYMP individuals in response to stimulation with either SYMP or ASYMP gB epitope peptides gB$_{342-350}$ and gB$_{561-569}$.

FIG. 4C summarizes the percentage of ASYMP and SYMP individuals who showed positive results for one or several CD8+ T cell functions following in vitro restimulation with either ASYMP or SYMP gB peptides. Overall, 95% of ASYMP individuals had HSV-specific CD8+ T cells with three to five functions, indicating their ability to maintain greater frequencies and display concurrent polyfunctional activities: 1) production of high levels of lytic granules upon TCR engagement (CD107a/b cytotoxic activity); 2) expression of IFN-γ (ELISPOT); 3) high proliferation (CFSE); 4) production of high levels of IL-2, IFN-γ, and TNF-α effector cytokines (or proinflammatory cytokines in the case of SYMP individuals); and 5) tetramer frequency (p<0.005). In contrast, only 32% of SYMP individuals had HSV-specific CD8+ T cells with three to five functions whereas most had just one function, indicating that CD8+ T cells from SYMP patients tended to be monofunctional and produced more inflammatory cytokines (p<0.005). Similar levels of HLA-A*02:01 expression were detected by FACS on the surface of antigen presenting cells (APCs) (both dendritic cells and macrophages) derived from SYMP and ASYMP individuals (data not shown). This result indicates that the apparent polyfunctionality of CD8+ T cells detected in ASYMP individuals is not a result of a high level of expression of HLA-A0201 molecules on their APCs, but rather to an intrinsic multifunctionality of CD8+ T cells specific to ASYMP epitopes.

Immunization with "Asymptomatic" Epitopes Induced a CD8+ T Cell-Dependent Protective Immunity against Ocular Herpes in "Humanized" HLA-A*02:01 Transgenic Mice. To evaluate whether immunization with ASYMP CD8+ T cell epitopes confer protection against ocular herpes, groups of susceptible HLA-A*02:01 transgenic humanized mice (n=10 mice/group, BALB/c genetic background) described in Example 14 were immunized s.c. twice, 21 days apart with the ASYMP epitopes $gB_{342\text{-}350}$ and $gB_{561\text{-}569}$ (ASYMP group) or with SYMP epitopes $gB_{183\text{-}191}$ and $gB_{441\text{-}449}$ (SYMP group) as described in Example 16. These were delivered together with the CD4+ T helper PADRE epitope and emulsified in $CpG_{1826}$ adjuvant. As negative control, mock-immunized mice received adjuvant alone (control group or mock). Two weeks after the second and final immunization, animals from all groups received an ocular HSV-1 challenge ($2\times10^5$ PFU, McKrae strain). Of note, the sequences of both SYMP and ASYMP epitopes are highly conserved between HSV-1 and HSV-2 strains; however, no significant homology exists between the amino acid sequences of the 10 HSV-1 gB T cell epitopes studied and the gB amino acid sequences of varicella zoster virus, EBV, and CMV.

The pathology clinical scores observed in the ASYMP group were significantly lower than those observed in the SYMP group and the control group (p=0.001 for all; FIG. 5A). In addition, significantly lower viral loads were detected on day 7 postinfection in eye swabs of the ASYMP group compared with the SYMP and control groups (p=0.01; FIG. 5B). All animals in the ASYMP group survived lethal infection (100%) compared with only 40% survival in the SYMP group and 0% in the control group (p<0.005; FIG. 5C).

Figure 5D:
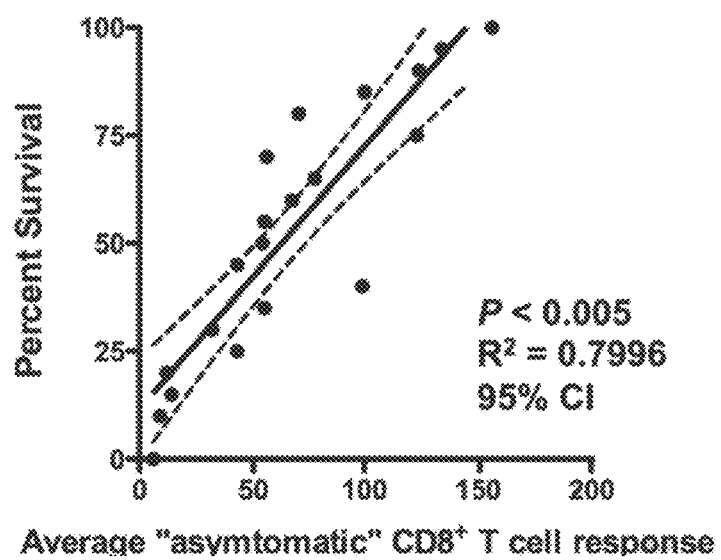
Figure 5E:
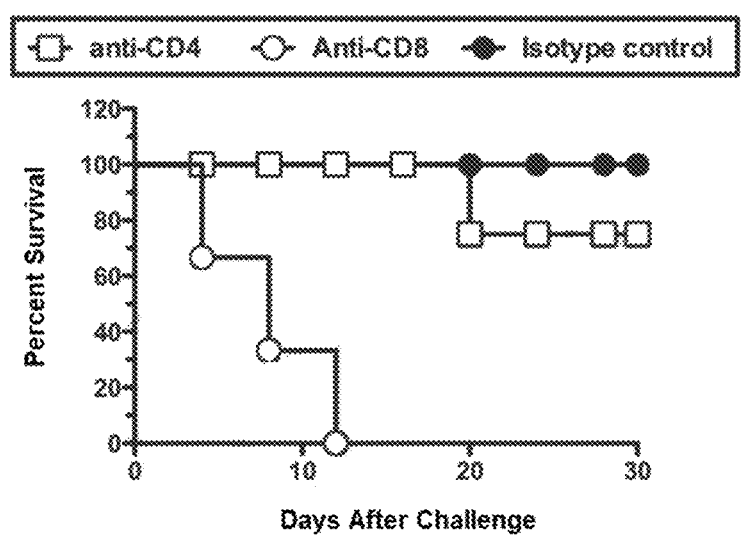

Overall, there was a positive correlation between survival and the number of ASYMP CD8+ T cells detected in the draining lymph node (FIG. 5D, p<0.005, $r^2$=0.7996, 95% confidence interval). Similar to what has been observed in ASYMP individuals, cultured CD8+ T cells from ASYMP group mice had significantly higher proportions of cells with simultaneous expression of three to five functions, whereas SYMP group mice had few or no de-tectable cells expressing more than three functions simultaneously (75.5 and 17.5%, respectively; p=0.005; not shown). To verify the involvement of CD8+ T cells in the observed protection against ocular HSV-1 challenge induced by immunization with the ASYMP CD8+ T cell epitopes, an in vivo depletion of either CD4+ or CD8+ T cells was performed in immunized mice before virus challenge using specific mAbs. As shown in FIG. 5E, depletion of CD8+ T cells, but not of CD4+ T cells, significantly abrogated protection against death induced by immunization with the ASYMP CD8+ T cell epitopes (p<0.005), indicating that CD8+ T cells, but not CD4+ T cells, were required for protection against lethal ocular herpes.

Altogether, these results indicate that immunization with ASYMP CD8+ T cell epitopes, but not ith SYMP epitopes, decreased ocular herpes disease, decreased virus replication, and protected against lethal ocular herpes in susceptible HLA transgenic mice.

EXAMPLE 1

Human Study Population. Over the course of the last decade, we have screened a total of 525 individuals for HSV-1 and HSV-2 seropositivity. Among these individuals, a cohort of 207 immunocompetent individuals, with an age range of 18-65 years (median, 32 years), who were seropositive for HSV-1 were enrolled in the current study. Three hundred eighty-five individuals were white, 140 were non-white (African, Asian, Hispanic, and others), 274 were females, and 251 were males. All patients were negative for HIV, hepatitis B virus, and had no history of immunodeficiency. Two hundred eighteen patients were HSV-1 seropositive or HSV-1/HSV-2seropositive, among whom 208 patients were healthy and ASYMP (individuals who have never had any recurrent herpetic disease). Ten patients were HSV-1 seropositive SYMP, and suffered frequent and severe herpetic oral and/or orofacial lesions. At the time of blood collection, however, the SYMP patients had no recurrent disease (other than corneal scarring) and had no recurrences during the 30 days prior to blood collection. The SYMP patients had no ocular disease other than HSK, no history of recurrent genital herpes, were HSV-1seropositive, and were HSV-2seronegative. Patients were also excluded when they 1) had an active herpetic lesion, or had one in the past 30 days; 2) were seropositive for HSV-2; 3) were pregnant or breastfeeding; and/or 4) had ever taken acyclovir or related antiviral drugs or any immunosuppressive drugs. SYMP and ASYMP patient groups were matched for age, gender, serological status, and race. Sixty-nine healthy control individuals were seronegative for both HSV-1 and HSV-2 and had no history of herpetic disease. All subjects were enrolled at the University of California, Irvine under approved Institutional Review Boardapproved protocols (nos. 2003-3111 and 2009-6963). Written informed consent was received from all participants prior to inclusion in the study.

EXAMPLE 2

Bioinformatics Analyses. HSV-1 gB open reading frames used in this study were from strain 17 (National Center for Biotechnology Information, accession no. NC-001806). Candidate HLA-A*02:01restricted epitopes were identified using previously described software from the National Institutes of Health Bioinformatics and Molecular Analysis Section (Washington, D.C.; http://bimas.dcrt.nih.gov/molbio/hla_bind/) and the SYFPEITHI algorithm (http://www.syfpeithi.de/), Potential cleavage sites for human proteasome were identified using NetChop 3.0 (http://www.cbs.dtu.dk/services/NetChop/). MHC Pathway (http://www.mhc-pathway.net) was also employed in this screening.

EXAMPLE 3

Peptide Synthesis. HLA-A*02:01binding peptides from gB were synthesized by Magenex (San Diego, Calif.) on a 9050 Pep Synthesizer using solid-phase peptide synthesis and standard 9-fluorenylmethoxycarbonyl technology (PE Applied Biosystems, Foster City, Calif.). The purity of peptides was between 75 and 96%, as determined by reversed-phase HPLC (Vydac C18) and mass spectroscopy (Voyager MALDI-TOF system). Stock solutions were made at 1 mg/ml in 10% DMSO in PBS. All peptides were aliquoted and stored at −20° C. until assayed.

EXAMPLE 4

Binding with Soluble HLA-A*02:01 Molecules. Quantitative assays to measure binding of peptides to soluble HLA-A*02:01 molecules were based on inhibition of binding of a radiolabeled standard peptide. Briefly, 1-10 nM radiolabeled peptide was coincubated with 1 M-1 nM purified MHC and 1-3 µM human β2-microglobulin. After 2 days, binding of radiolabeled peptide to MHC class I molecules was determined by capturing MHC/peptide complexes on Greiner Lumitrac 600 microplates coated with W6/32 Ab and measuring bound counts per minutes using a TopCount microscintillation counter. Concentration of peptide yielding 50% inhibition of binding of radio-labeled probe peptide (IC50) was then calculated.

EXAMPLE 5

Stabilization of HLA-A*02:01 on Class I-HLAtransfected B X T Hybrid Cell Lines (T2 Cell Line). To determine whether synthetic peptides could stabilize HLA-A*02:01 molecule expression on the T2 cell surface, peptide-inducing HLA-A*02:01 upregulation on T2 cells was examined as described by (Chentoufi, A. et al., HLA-A*0201-restricted CD8$^+$ cytotoxic T lymphocyte epitopes identified from herpes simplex virus glyco-protein D. *J. Immunol.* 180: 426-437 (2008), the content of which is hereby incorporated by reference in its entirety. T$_2$ cells ($3\times10^5$/well) were incubated with different concentrations of individual gB peptide in 48-well plates for 18 hours at 26° C. Cells were then incubated at 37° C. for 3 hours in the presence of human β$_2$-microglobulin (1 µg/ml) and BD GolgiStop (5 µg/ml) to block cell surface expression of newly synthesized HLA-A*02:01 molecules. The cells were washed with FACS buffer (1% BSA and 0.1% sodium azide in PBS) and stained with anti-HLA-A2.1specific mAb BB7.2 (BD Pharmingen, San Diego, Cailf.) at 4° C. for 30 min. After incubation, the cells were washed with FACS buffer, fixed with 1% paraformaldehyde in PBS, and analyzed by flow cytometry using a BD LSR II (Becton Dickinson, Mountain View, Calif.). The acquired data, including mean fluorescence intensity (MFI), were analyzed with a FlowJo software version 9.5.2 (Tree Star). Percentage MFI increase was calculated as [(MFI with the given peptide−MFI without peptide)/(MFI without peptide)]×100. Each experiment was performed three times, and means±SD were calculated.

EXAMPLE 6

HLA Typing. HLA-A2 subtyping was performed using a commercial sequence-specific primer kit (SSPR1-A2; One Lambda, Canoga Park, Calif.) following the manufacturer's instructions. Briefly, genomic DNA extracted from PBMCs of HSV-seropositive SYMP and ASYMP individuals was analyzed using a Tecan DNA workstation from a 96-well plate with 2 µl volume per well, as described by Bunce, M., PCR-sequence-specific primer typing of HLA class I and class II alleles. *Methods Mol. Biol.* 210:143-171 (2003.), the content of which is hereby incorporated by reference in its entirety. The yield and purity of each DNA sample were determined using a UV spectrophotometer. The integrity of DNA samples was determined by agarose gel electrophoresis. Each DNA sample was subjected to multiple, small-volume PCR reactions using primers specific to areas of the genome surrounding the single point mutations associated with each allele. Only primers that matched the specific sequence of a particular allele would amplify a product. The PCR products were subsequently electrophoresed on a 2.5% agarose gel with ethidium bromide, and the pattern of amplicon generation was analyzed using HLA Fusion software (One Lambda). Additionally, the HLA-A2 status was confirmed by staining PBMCs with 2 µl antiHLA-A2 mAb BB7.2 (BD Pharmingen) at 4° C. for 30 min. The cells were washed, acquired on a BD LSR II, and analyzed using FlowJo software version 9.5.2 (Tree Star).

EXAMPLE 7

PBMC isolation. Healthy individuals (negative for HIV, hepatitis B virus, and with or without any HSV infection history) were recruited at the University of California Irvine Institute for Clinical and Translational Science. Between 40 and 100 ml blood was drawn into yellow-top Vacutainer tubes (Becton Dickinson). The serum was isolated and stored at −80° C. for detection of antiHSV-1 and antiHSV-2 Abs, as previously described by Chentoufi, A. et al., Asymptomatic human $CD4^+$ cytotoxic T-cell epitopes identified from herpes simplex virus glycoprotein B. *J. Virol.* 82: 11792-11802 (2008), the content of which is hereby incorporated by reference in its entirety. PBMCs were isolated by gradient centrifugation using leukocyte separation medium (Cellgro, Manassas, Va.). The cells were washed in PBS and resuspended in complete culture medium consisting of RPMI 1640 medium containing 10% FBS (Gemini Bio-Products, Woodland, Calif.) supplemented with 1× penicillin/L-glutamine/streptomycin, 1× sodium pyruvate, 1× non-essential amino acids, and 50 µM 2-ME (Life Technologies, Rockville, Md.). Aliquots of freshly isolated PBMCs were also cryopreserved in 90% FCS and 10% DMSO in liquid nitrogen.

EXAMPLE 8

T Cell Proliferation Assay. $CD8^+$ T cell proliferation was measured using a CFSE assay as we described by Chentoufi, A et al., A novel HLA (HLA-A*0201) transgenic rabbit model for preclinical evaluation of human $CD8^+$ T cell epitope-based vaccines against ocular herpes. *J. Immunol.* 184: 2561-2571 (2010), the content of which is hereby incorporated by reference in its entirety. Briefly, PBMCs were labeled with CFSE (2 µM) and incubated for 5 days with or without individual gB peptide (10 µg/ml). As a positive control, 2 µg/ml PHA was used to stimulate T cells for 3 days. The cells were then washed and stained with PE-conjugated mAbs specific to human CD8 molecules (clone HIT8A; BD Pharmingen). The numbers of dividing $CD8^+$ T cells per 300,000 total cells were analyzed by FACS. Their absolute number was calculated using the following formula: number of events in $CD8^+/CFSE^+$ cells× number of events in gated lymphocytes/number of total events acquired.

EXAMPLE 9

Flow cytometry analysis. For each stimulation condition, at least 500,000 total events were acquired on a BD LSR II, and data analysis was performed using FlowJo version 9.5.2 (Tree Star). PBMCs were analyzed by flow cytometry after staining with fluorochrome-conjugated human specific mAbs. FITC-conjugated CD8 (clone HIT8A) and FITC-conjugated HLA-A2 (clone BB7.2) were purchased from BD Pharmingen. PE-conjugated gB peptide/tetramer complexes were gifted by the National Institutes of Health Tetramer Facility. A total of $10^6$ PBMCs were stained in PBS containing 1% BSA and 0.1% sodium azide (FACS buffer) for 45 minutes at 4° C. followed by three washes in FACS buffer and fixed in 1% paraformaldehyde. The gating strategy was similar to that by Chentoufi, A. et al., HLA-A*0201-restricted $CD8^+$ cytotoxic T lymphocyte epitopes identified from herpes simplex virus glycoprotein D. *J. Immunol.* 180: 426-437 (2008), the content of which is hereby incorporated by reference in its entirety. We gated on single cells, dump$^-$ cells, viable cells (aqua blue$^-$), lymphocytes, $CD3^+$ cells, and $CD8^+$ cells before gating on functional cells. Reported data have been corrected for background based on the negative (no peptide) control where appropriate, and only responses with a total frequency >0.10% of total $CD8^+$ T cells (after background subtraction) were considered to be positive responses.

EXAMPLE 10

Tetramer/gB Peptide Complexes Staining. Fresh PBMCs were analyzed for the frequency of $CD8^+$ T cells recognizing the gB peptide/tetramer complexes, as previously described Nesburn, A. et al., Topical/mucosal delivery of sub-unit vaccines that stimulate the ocular mucosal immune system. *Ocul. Surf* 4: 178-187 (2006) and BenMohamed, L. et al., Lipopeptide vaccines: yesterday, today, and tomorrow. *Lancet Infect. Dis.* 2: 425-431 (2002), the contents of which are hereby incorporated by reference in their entireties. The cells were incubated with gB peptide/tetramer complex for 30-45 minutes at 37° C. The cell preparations were then washed with FACS buffer and stained with FITC-conjugated anti-human CD8 mAb (BD Pharmingen). The cells were washed and fixed with 1% paraformaldehyde in PBS. The cells were then acquired on a BD LSR II and data were analyzed using FlowJo version 9.5.2 (Tree Star).

EXAMPLE 11

IFN-γ-ELISPOT Assays. gB-specific IFN-γ-producing $CD8^+$ T cells were characterized using ELISPOT. T cell stimulation was measured by IFN-γ production in peptide-stimulated PBMCs using a BD IFN-γ-ELISPOT kit (BD Pharmingen). Briefly, $5×10^5$ PBMCs were stimulated with 20 µM individual gB peptides for 5 days. Then, activated PBMCs were harvested, washed, and restimulated with the gB peptides for 24 hours in IFN-γ-ELISPOT plates (Millipore) that had been previously coated with anti-human IFN-γ capture Ab in a humidified incubator at 37° C. with 5% $CO_2$. The spot-forming cells were developed as described by the manufacturer (BD IFN-γ-ELISPOT kit; BD Pharmingen) and counted under stereoscopic microscope. Average spot counts for duplicate wells were calculated and background from wells with cells in medium only was subtracted.

EXAMPLE 12

Multiplex Cytokine Array. Fresh PBMCs ($5×10^5$ cells) were stimulated in a 96-well round-bottom plate with or without gB peptides for 24, 48, or 96 hours. Supernatants were collected after 24, 48, or 96 hoursof stimulation. Production of six different cytokines (IL-2, IL-6, IL-8, IL-17, IFN-γ, and TNF-α) was assayed using multiplex cytokine arrays (BioLegend) per the manufacturer's protocols. Samples were acquired on a Labscan 100 analyzer (Luminex) using Bio-Plex manager 6.0 software (Bio-Rad). Background levels were determined from nonstimulated PBMCs.

EXAMPLE 13

CD107 Cytotoxicity Assay. To detect cytolytic CD8+ T cells recognizing gB peptides in freshly activated and in vitroactivated PBMCs, we performed CD107a/b cytotoxicity assay. The CD107 assay was performed as described by Gilchuk, P. et al., Discovering naturally processed antigenic determinants that confer protective T cell immunity. *J. Clin. Invest.* 123: 1976-1987 (2013) and Moutaftsi, M. et al., Correlates of protection efficacy induced by vaccinia virus-specific CD8+ T-cell epitopes in the murine intranasal challenge model. *Eur, J. Immunol.* 39: 717-722 (2009), the entire contents of which are hereby incorporated by reference in their entireties, with a few modifications. On the day of the assay, nonstimulated or in vitro gB peptide-stimulated PBMCs were incubated at 37° C. for 6 hours in a 96-well plate with BD GolgiStop (BD Biosciences), costimulatory anti-CD28 and anti-CD49d Abs (1 µg/ml), and 10 ml CD107a-FITC and CD107b-FITC. At the end of the incubation period the cells were harvested into separate tubes and washed twice with FACS buffer then stained with PE-conjugated anti-human CD8 for 30 minutes at 4° C. The cells were then washed again, fixed, and 500,000 total events were acquired on a BD LSR II, and data analysis was performed using FlowJo version 9.5.2 (Tree Star).

EXAMPLE 14

HLA-A*02:01 Transgenic Mice. HLA-A*02:01 transgenic mice provided by Dr. Lemonier (Pasteur Institute) were bred at the University of California Irvine. These mice represent the $F_1$ generation resulting from a cross between HLA-A*02:01/$K^b$ transgenic mice (expressing a chimeric gene consisting of the 1 and 2 domains of HLA-A*02:01 and the 3 domain of H-2$K^b$) created on the BALB/c genetic background. Genotype of the HLA transgenic mice used in this study was confirmed as HLA-A*02:01, the most common A*02 subtype, supporting that the immunogenic SYMP versus ASYM peptide epitopes reported in this study are likely presented by the HLA-A*02:01 molecule. All animal studies were conducted in facilities approved by the Association for Assessment and Accreditation of Laboratory Animal Care and according to Institutional Animal Care and Use Committee-approved animal protocol (no. 202-2372). All studies have been approved by the University of California Irvine review Institutional Animal Care and Use Committee.

EXAMPLE 15

Virus Production. HSV-1 (strain McKrae) was used in this study; and was grown and titrated on rabbit skin (RS) cells. UV-inactivated HSV-1 was generated as previously described Zhang, X. et al., Targeting the genital tract mucosa with a lipopeptide/recombinant adenovirus prime/boost vaccine induces potent and long-lasting CD8+ T cell immunity against herpes: importance of MyD88. *J. Immunol.* 189: 4496-4509 (2012), the entire content of which is hereby incorporated by reference in its entirety. HSV inactivation was confirmed by the inability to produce plaques when tested on RS cells.

EXAMPLE 16

Immunization of "Humanized" HLA Transgenic Mice with SYMP and ASYMP Peptide Epitopes and Ocular Herpes Challenge. Three groups of age-matched female HLA-A*02:01 transgenic mice (n=10 each) were immunized s.c. with the ASYMP CD8+ T cell human epitopes ($gB_{342-350}$ and $gB_{561-569}$) delivered with the CD4+ T cell PADRE epitope emulsified in $CpG_{1826}$ adjuvant (ASYMP), with the SYMP CD8+ T cell human epitopes ($gB_{183-191}$ and $gB_{441-449}$) delivered with the CD4+ T cell PADRE epitope emulsified in $CpG_{1826}$ adjuvant (SYMP), or with the $CpG_{1826}$ adjuvant alone (mock) on days 0 and day 21. All immunizations were carried out with 100 µM each peptide.

A preliminary experiment was conducted to determine the $LD_{50}$ of strain McKrae in naive HLA-A*02:01 transgenic mice following ocular challenge. Two×$LD_{50}$ was then used in peptide-immunized and mock-immunized mice to determine the protective efficacy of SYMP and ASYMP epitopes against lethal ocular herpes infection and disease. Two weeks after the final immunization, mice received an ocular HSV-1 challenge with 2×10$^5$ PFU (strain McKrae). The corneas were inoculated, without scarification, with the virus in a 4 µl tissue culture medium placed gently and topically on the corneas of immunized and control mice, as previously described by Chentoufi, A. et al. (2008). Control mice were inoculated using mock samples of virus.

EXAMPLE 17

Monitoring of Ocular Herpes Infection and Disease. Animals were examined for signs of ocular disease by slit lamp. Clinical assessments were made immediately before inoculation and on days 1, 4, 7, 10, 14, and 21 thereafter. The examination was performed by investigators blinded to the treatment regimen of the mice and scored according to a standard 0-4 scale: 0, no disease; 1, 25%; 2, 50%; 3, 75%; and 4, 100% staining, as previously described by Chentoufi, A. et al, (2008). To quantify replication and clearance of HSV-1 from the eyes, mice were swabbed daily with moist, type 1 calcium alginate swabs. Swabs were placed in 1.0 ml titration media (Media 199, 2% penicillin/streptomycin, 2% newborn calf serum) and frozen at −80° C. until titrated on RS cell monolayers as described by Chentoufi, A. et al. (2008). Mice were also examined for survival in a window of 30 days after challenge, as described by Chentoufi, A. et al. (2008).

EXAMPLE 18

Statistical Analyses. Data for each assay were compared by ANOVA and a Student t test using GraphPad Prism 5 software (GraphPad Software, San Diego, Calif.). Differences between the groups were identified by ANOVA and multiple comparison procedures, as described by Zhang, X. et al., A genital tract peptide epitope vaccine targeting TLR-2 efficiently induces local and systemic CD8+ T cells and protects against herpes simplex virus type 2 challenge. *Mucosal Immunol.* 2: 129-143 (2009), the content of which is hereby incorporated by reference in its entirety. Data were expressed as the means±SD. Results were considered to be statistically significant at p<0.05.

The skilled artisan will recognize the interchangeability of various features from different embodiments. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. An isolated immunogenic peptide consisting of an amino acid sequence selected from the group consisting of NLLTTPKFT (SEQ ID NO: 5) and RMLGDVMAV (SEQ ID NO: 9).

2. An immunogenic composition comprising the peptide of claim 1, wherein the immunogenic composition is capable of inducing in a mammal a CD8+ T cell-dependent protective immunity against an HSV-1 infection, an HSV-2 infection, an HSV-1 condition, an HSV-2 condition, or combinations thereof.

3. The composition of claim 2, further comprising an adjuvant selected from the group consisting of $CpG_{1826}$ and lipopeptides.

4. The composition of claim 2, further comprising a PADRE epitope.

5. A method, of inducing in a mammal a CD8+ T cell-dependent protective immunity against an HSV-1 infection, HSV-2 infection, an HSV-1 condition, an HSV-2 condition, or combinations thereof, comprising administering to the mammal the immunogenic composition of claim 2.

6. A synthetic immunogenic peptide consisting of an amino acid sequence selected from the group consisting of NLLTTPKFT (SEQ ID NO: 5) and RMLGDVMAV (SEQ ID NO: 9).

7. An immunogenic composition comprising the peptide of claim 6, wherein the immunogenic composition is capable of inducing in a mammal a CD8+ T cell-dependent protective immunity against an HSV-1 infection, an HSV-2 infection, an HSV-1 condition, an HSV-2 condition, or combinations thereof.

8. The composition of claim 7, further comprising an adjuvant selected from the group consisting of $CpG_{1826}$ and lipopeptides.

9. The composition of claim 7, further comprising a PADRE epitope.

10. A method, of inducing in a mammal a CD8+ T cell-dependent protective immunity against an HSV-1 infection, HSV-2 infection, an HSV-1 condition, an HSV-2 condition, or combinations thereof, comprising administering to the mammal the immunogenic composition of claim 7.

11. A method, of inducing in a mammal a CD8+ T cell-dependent protective immunity against an HSV-1 infection, HSV-2 infection, an HSV-1 condition, an HSV-2 condition, or combinations thereof, comprising administering to the mammal an immunogenic composition comprising a synthetic peptide having an amino acid sequence selected from the group consisting of NLLTTPKFT (SEQ ID NO: 5) and RMLGDVMAV (SEQ ID NO: 9).

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Ala Leu Leu Gly Leu Thr Leu Gly Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Thr Met Tyr Tyr Lys Asp Val Thr Val
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gly Ile Phe Glu Asp Arg Ala Pro Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Phe Val Leu Ala Thr Gly Asp Phe Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Asn Leu Leu Thr Thr Pro Lys Phe Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Leu Leu Thr Thr Pro Lys Phe Thr Val
1               5

```
<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Tyr Leu Ala Asn Gly Gly Phe Leu Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Phe Leu Ile Ala Tyr Gln Pro Leu Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Arg Met Leu Gly Asp Val Met Ala Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Thr Met Leu Glu Asp His Glu Phe Val
1               5
```